(12) United States Patent
Privitera et al.

(10) Patent No.: US 7,828,795 B2
(45) Date of Patent: Nov. 9, 2010

(54) SURGICAL ABLATION AND PACING DEVICE

(75) Inventors: Salvatore Privitera, Mason, OH (US);
Keith Edward Martin, Mason, OH (US); Michael Dawson Hooven, Cincinnati, OH (US)

(73) Assignee: AtriCure, Inc., West Chester, OH (US)

( * ) Notice: Subject to any disclaimer, the term of this patent is extended or adjusted under 35 U.S.C. 154(b) by 962 days.

(21) Appl. No.: 11/363,707

(22) Filed: Feb. 28, 2006

(65) Prior Publication Data

US 2006/0161151 A1     Jul. 20, 2006

Related U.S. Application Data

(63) Continuation-in-part of application No. 11/037,543, filed on Jan. 18, 2005, now abandoned.

(60) Provisional application No. 60/699,679, filed on Jul. 15, 2005.

(51) Int. Cl.
*A61B 18/14* (2006.01)
*A61B 5/04* (2006.01)
*A61N 1/05* (2006.01)

(52) U.S. Cl. ............................ 606/41; 607/122; 600/374

(58) Field of Classification Search .................. 606/41, 606/48–50; 607/122; 600/374
See application file for complete search history.

(56) References Cited

U.S. PATENT DOCUMENTS

| | | | |
|---|---|---|---|
| 4,026,303 A | 5/1977 | Babotai | |
| 4,074,718 A | 2/1978 | Morrison, Jr. | |
| 5,230,349 A | 7/1993 | Langberg | |
| 5,398,683 A | 3/1995 | Edwards et al. | |
| 5,478,347 A * | 12/1995 | Aranyi | 606/170 |
| 5,484,435 A * | 1/1996 | Fleenor et al. | 606/46 |
| 5,558,671 A | 9/1996 | Yates | |

(Continued)

FOREIGN PATENT DOCUMENTS

WO   WO 2004/103195   12/2004

(Continued)

OTHER PUBLICATIONS

PCT International Search Report, PCT/US2005/044201, International filind date Dec. 6, 2005, mailed May 5, 2006.

(Continued)

*Primary Examiner*—Linda C Dvorak
*Assistant Examiner*—Benjamin Lee
(74) *Attorney, Agent, or Firm*—Cook Alex Ltd.

(57) ABSTRACT

A surgical device has an integral first tip having pair of electrodes configured to ablate tissue using electric energy. A second tip has a pair of electrodes configured to provide pacing signals to a heart and/or to sense electrical signals passing through heart tissue. The second tip is configured to snap onto the first tip, such that the same device may be used for ablation, pacing, and sensing. Alternatively, the second tip may be integral with the device and the first tip configured to snap onto the second tip. Alternatively, a single integral tip of the surgical device may be used for ablation, pacing, and sensing. Such a multipurpose tip may comprise a plurality of electrode pairs or an array of electrodes. A user interface on the device or elsewhere may be operable to provide selectable modes for selectively varying properties of signals communicated to the electrodes.

16 Claims, 8 Drawing Sheets

U.S. PATENT DOCUMENTS

| | | | | |
|---|---|---|---|---|
| 5,626,578 | A | * | 5/1997 | Tihon .......................... 606/48 |
| 5,634,924 | A | | 6/1997 | Turkel et al. |
| 5,688,267 | A | | 11/1997 | Panescu et al. |
| 5,810,764 | A | * | 9/1998 | Eggers et al. ................. 604/23 |
| 5,891,140 | A | * | 4/1999 | Ginn et al. .................... 606/48 |
| 5,967,976 | A | | 10/1999 | Larsen et al. |
| 5,971,980 | A | | 10/1999 | Sherman |
| 6,086,586 | A | | 7/2000 | Hooven |
| 6,099,524 | A | | 8/2000 | Lipson et al. |
| 6,162,216 | A | | 12/2000 | Guziak et al. |
| 6,167,291 | A | * | 12/2000 | Barajas et al. .............. 600/374 |
| 6,228,080 | B1 | | 5/2001 | Gines |
| 6,309,388 | B1 | * | 10/2001 | Fowler ........................ 606/45 |
| 6,332,881 | B1 | | 12/2001 | Carner et al. |
| 6,391,024 | B1 | * | 5/2002 | Sun et al. ..................... 606/34 |
| 6,398,779 | B1 | | 6/2002 | Buysse et al. |
| 6,464,696 | B1 | | 10/2002 | Oyama et al. |
| 6,511,476 | B2 | | 1/2003 | Hareyama |
| 6,517,536 | B2 | | 2/2003 | Hooven et al. |
| 6,695,839 | B2 | | 2/2004 | Sharkey et al. |
| 6,730,082 | B2 | | 5/2004 | Messing et al. |
| 6,743,225 | B2 | | 6/2004 | Sanchez et al. |
| 7,147,638 | B2 | | 12/2006 | Chapman et al. |
| 7,169,146 | B2 | | 1/2007 | Truckai et al. |
| 2001/0037108 | A1 | * | 11/2001 | Blocher et al. ................ 606/48 |
| 2002/0032441 | A1 | | 3/2002 | Ingle et al. |
| 2003/0014043 | A1 | * | 1/2003 | Henry et al. ................... 606/34 |
| 2003/0055420 | A1 | | 3/2003 | Kadhiresan et al. |
| 2003/0181904 | A1 | | 9/2003 | Levin et al. |
| 2003/0181965 | A1 | | 9/2003 | Levy et al. |
| 2003/0216733 | A1 | | 11/2003 | McClurken et al. |
| 2003/0220639 | A1 | | 11/2003 | Chapelon et al. |
| 2004/0030331 | A1 | | 2/2004 | Thomas et al. |
| 2004/0082860 | A1 | | 4/2004 | Haissaguerre |
| 2004/0082946 | A1 | | 4/2004 | Malis et al. |
| 2004/0092926 | A1 | | 5/2004 | Hoey et al. |
| 2004/0133251 | A1 | | 7/2004 | Altshuler et al. |
| 2004/0181214 | A1 | | 9/2004 | Garabedian et al. |
| 2004/0193148 | A1 | | 9/2004 | Wham et al. |
| 2005/0033283 | A1 | | 2/2005 | Hooven |
| 2005/0070896 | A1 | | 3/2005 | Daniel et al. |
| 2005/0080411 | A1 | * | 4/2005 | Ouchi .......................... 606/45 |
| 2006/0161149 | A1 | | 7/2006 | Privitera et al. |
| 2006/0161151 | A1 | | 7/2006 | Privitera et al. |
| 2006/0217701 | A1 | | 9/2006 | Young et al. |

OTHER PUBLICATIONS

PCT Written Opinion of the International Searching Authority, PCT/US2005/044201, International filing date Dec. 6, 2005.
Partial European Search Report, issued in EP Application No. 07 252279.0, dated Sep. 5, 2007.
Extended European Search Report issued in EP Application No. 07 252279.02, dated Nov. 20, 2007.
PCT International Preliminary Report on Patentability and PCT Written Opinion of the International Searching Authority, Sep. 2, 2008, International Application No. PCT/US2007/004908.
PCT International Search Report, PCT/US2007/004908, Feb. 23, 2007.
PCT Written Opinion of the International Searching Authority, PCT/US2007/004908, Feb. 23, 2007.
ACC/AHA/ESC Pocket Guidelines, Mar. 2002.
Armour, J.A., et al., "Gross and Microscopic Anatomy of the Human Intrinsic Cardiac Nervous System", The Anatomical Record, Feb. 1997, pp. 289-298, vol. 247, No. 2, Wiley-Liss, Inc.
Blackshear, J.L., et al., Thoracoscopic extracardiac obliteration of the left atrial appendage for stroke risk reduction in atrial fibrillation, J Am Coll Cardiol, Oct. 1, 2003, pp. 1249-1252, vol. 42, No. 7.
Chen, S.A., et al., "Initiation of atrial fibrillation by ectopic beats originating from the pulmonary veins: Electrophysiological charac-teristics, pharmacological responses, and effects of radiofrequency ablation", Circulation, 1999, pp. 1879-1886, vol. 100.
Cox, J.K., et al., "Electrophysiologic basis, surgical development, and clinical results of the maze procedure for atrial flutter and atrial fibrillation", Adv. Car Surg, 1995, pp. 1-67, vol. 6.
Cox, J.L., "Impact of the maze procedure on the stroke rate in patients with atrial fibrillation", J. Thorac Cardiovasc Surg., Nov. 1999, pp. 833-840, vol. 118, No. 5.
Cox, J.L., et al., "Current status of the maze procedure for the treatment of atrial fibrillation", Semin. Thorac Cardiovasc Surg, 2000, pp. 15-19, vol. 12.
Cox, J.L., et al., "New surgical and catherized modifications of the Maze procedure," Semin Thorac Cardiovasc Surg, 2000, pp. 68-73, vol. 12.
Cox, J.L., et al., "The development of the maze procedure for the treatment of atrial fibrillation", Semin Thorac Cardiovasc Surg, 2000, pp. 2-14, vol. 12.
Damiano, R.J., Jr., et al., "The long-term outcome of patients with coronary disease and atrial fibrillation undergoing the Cox maze procedure", J Thorac Cardiovasc Surg., Dec. 2003, pp. 2016-2021, vol. 126, No. 6.
Deneke, T., et al., "Antiarrhythmic surgery to cure atrial fibrillation—subgroups and postoperative management", Card Electrophysiol Rev, Sep. 2003, pp. 259-263, vol. 7, No. 3.
Deneke, T., et al., "Efficacy of an additional MAZE procedure using cooled-tip radiofrequency ablation in patients with chronic atrial fibrillation and mitral valve disease. A randomized prospective trial", Eur Heart J., Apr. 2002, pp. 558-566, vol. 23, No. 7.
Di Tullio, M.R., et al., "Mechanisms of cardioembolic stroke", Curr Cardiol Rep., 2002, pp. 141-148, vol. 4.
Doshi, R.N., et al., "Relation between Ligament of Marshall and adrenergic atrial tachyarrhythmia", Circulation, Aug. 24, 1999, pp. 876-883, vol. 100, No. 8.
Feinberg, W.M., et al., "Prevalence, age distribution and gender of patients with atrial fibrillation: analysis and implications," Arch Intern Med., 1995, pp. 469-473, vol. 155.
Ganjoo, A.K., "A Novel Approach to the Prevention of Thromboembolism in Atrial Fibrillation", Tex Heart Inst, J., 2001, p. 163, vol. 28, No. 2.
Garrido, M.J., et al., "Minimally Invasive Surgery for Atrial Fibrillation: Toward a Totally Endoscopic, Beating Heart Approach", J Card Surg., 2004, pp. 216-220, vol. 19.
Gaynor, S.L., et al., "A prospective, single-center clinical trial of a modified Cox maze procedure with bipolar radiofrequency ablation", The Journal of Thoracic and Cardiovascular Surgery, pp. 535-542, vol. 128, No. 4, 2004.
Gillinov, A.M., et al., "Atrial fibrillation: current surgical options and their assessment", Ann Thorac Surg., 2002, pp. 2210-2217, vol. 74.
Gillinov, A.M., et al., "AtriCure bipolar radiofrequency clamp for intra-operative ablation of atrial fibrillation", Ann Thorac Surg, 2002, pp. 2165-2168, vol. 74.
Gillinov, A.M., et al., "Bipolar radiofrequency to ablate atrial fibrillation in patients undergoing mitral valve surgery", Heart Surg Forum, 2004, pages , vol. 7, No. 2.
Haissaguere, M. et al., "Spontaneous initiation of atrial fibrillation by ectopic beats originating in the pulmonary veins", New England Journal of Medicine 1998, pp. 659-666, vol. 339.
Haissaguerre, M., et all, "Electrophysiological breakthroughs from the left atrium to the pulmonary veins", Circulation, Nov. 14, 2000, pp. 2463-2465, vol. 102, No. 20.
Haissaguerre, M., et al., "Electrophysiological end point for catheter ablation of atrial fibrillation initiated from multiple pulmonary venous foci.", Circulation, 2000, pp. 1409-1417, vol. 101.
Haissaguerre, M., et al., "Sites of recurrences after catheter ablation of pulmonary vein initiated atrial; fibrillation", NASPE, 2000, p. 583, vol. 23.
Johnson, W.D., et al., "The left atrial appendage: our most lethal human attachment! Surgical implications", Eur J Cardiothorac Surg., Jun. 2000, pp. 718-722, vol. 17, No. 6.
Kalil, R.A., et al., "Assessment of thromboembolism after the Cox-Maze procedure for chronic atrial fibrillation secondary to mitral valve lesion", Arq Bras Cardiol., Apr. 2002, pp. 374-381, vol. 78, No. 4.

Kress, D.C., et al., "Validation of a left atrial lesion pattern for intraoperative ablation of atrial fibrillation", Ann Thorac Surg, 2002, pp. 1160-1168, vol. 73.

Lloyd-Jones, D.M., et al., Lifetime Risk for Development of Atrial Fibrillation—The Framingham Heart Study, Circulation, 2004, pp. 1042-1046, vol. 110.

Martin, A., et al., "Five-year follow-up of 101 elderly subjects by means of long-term ambulatory cardiac monitoring", Eur Heart J., 1984, pp. 592-596, vol. 5.

McCarthy, P.M., et al., "The Cox-Maze procedure: the Cleveland Clinic experience", Semin Thorac Cardiovasc Surg., 2000, pp. 25-29, vol. 12.

Melo, J.Q., et al., "Atrial Ablation for the Surgical Treatment of Atrial Fibrillation: Principles and Limitations", J Card Surg, 2004, pp. 207-210, vol. 19.

Mokadam, N.A., et al., "A prospective multicenter trial of bipolar radiofrequency ablation for atrial fibrillation: early results", Ann Thorac Surg., Nov. 2004, pp. 1665-1670, vol. 78, No. 5.

Nademanee, K., et al., "A new approach for catheter ablation of atrial fibrillation: mapping of the electrophysiologic substrates", J Am Coll Cardiol., Jun. 2, 2004, pp. 2044-2053, vol. 43, No. 11.

Nakagawa, H., et al., "Catheter ablation of cardiac autonomic nerves for prevention of atrial fibrillation in a canine model", Heart Thythm, 2004, vol. 1, S10 (Abstract 31).

Pappone C., et al., "Circumferential radiofrequency ablation of pulmonary vein ostia: A new anatomical approach for curing atrial fibrillation", Circulation, 2000, pp. 2619-2628, vol. 102.

Pappone, C., et al., "Atrial electroanatomic remodeling after circumferential radiofrequency pulmonary vein ablation: efficacy of an anatomic approach in a large cohort of patients with atrial fibrillation", Circulation, Nov. 20, 2001, pp. 2539-2544, vol. 104, No. 21.

Pappone, C., et al., "Pulmonary Vein Denervation Enhances Long-Term Benefit After Circumferential Ablation for Paroxysmal Atrial Fibrillation", Circulation, Jan. 27, 2004, pp. 327-334, vol. 109, No. 3, American Heart Association.

Patterson, E., et al., "Reentrant tachycardia elicited by acetylcholine from isolated canine pulmonary veins", Circulation, 2003, p. IV-149, vol. 108, (Abstract).

Patwardham, A.M., et al., "Radiofrequency modified maze procedure for chronic atrial fibrillation", Ind J Thorac Cardiovasc Surg., 2003, pp. 136-140, vol. 19.

Peters, N.S., et al., "Atrial Fibrillation: strategies to control, combat and cure", Lancet, 2002, pp. 593-603, vol. 359.

Prasad, S.M., et al, "Epicardial ablation on the beating heart: progress towards an off-pump maze procedure," Heart Surg Forum, 2001, pp. 100-104, vol. 5.

Prasad, S.M., et al., "Chronic transmural atrial ablation by using bipolar radiofrequency energy on the beating heart", J Thorac and Cardiovasc. Surg., 2002, pp. 708-713, vol. 124.

Prasad, S.M., et al., "Physiological consequences of bipolar radiofrequency energy on the atrial and pulmonary veins: a chronic animal study", Ann Thorac Surg., 2003, pp. 836-842, vol. 76.

Prasad, S.M., et al., "The Cox maze III procedure for atrial fibrillation: long-term efficacy in patients undergoing lone versus concomitant procedures", J Thorac Cardiovasc Surg., Dec. 2003, pp. 1822-1828, vol. 126, No. 6.

Raman, J., et al., "Surgical radiofrequency ablation of both atria for atrial fibrillation: results of a multicenter trial.", J Thorac Cardiovasc Surg., Nov. 2003, pp. 1357-1366, vol. 126, No. 5.

Ryan, W.H., et al., "Experience with Various Surgical Options for the Treatment of Atrial Fibrillation", The Heart Surgery Forum #2004, 2004, pp. 1013-1017, vol. 7, No. 4.

Saad, E.B., et al., "Pulmonary vein stenosis after catheter ablation of atrial fibrillation: Emergency of a new clinical syndrome", Annals of Internal Medicine, Apr. 2003, pp. 634-639, vol. 138, No. 8.

Scherlag, B.J., et al., "Stimulation of the 'sino atrial' fat pad converts focal pulmonary vein firing into atrial fibrillation in the dog heart", Circulation, 2003, pp. IV-85, vol. 108 (Abstract).

Sie, H.T., et al., "Long-term results of irrigated radiofrequency modified maze procedure in 200 patients with concomitant cardiac surgery: six years experience", Ann Thorac Surg., Feb. 2004, pp. 512-516 (discussion pp. 516-517), vol. 77, No. 2.

Sie, H.T., et al., "Radiofrequency modified maze in patients with atrial fibrillation undergoing conmitant cardiac surgery", J Thorac Cardiovasc Surg., 2001, pp. 249-256, vol. 122.

Sundt, T.M., III, et al., "The maze procedure for cure of atrial fibrillation", Cardiol Clin., 1997, pp. 739-748, vol. 15.

Tomita, T., M.D., et al., "Role of Autonomic Tone in the Initiation and Termination of Paraxysmal Atrial Fibrillation in Patients Without Structural Heart Disease", Journal of Cardiovascular Electrophysiology, Jun. 2003, pp. 559-564, vol. 14, No. 6.

Treseder, A.S., et al., "Atrial fibrillation and stroke in elderly hospitalized patients", Age Aging, 1986, pp. 89-92, vol. 15.

Wharton, J.M., "Ablation of Atrial Fibrillation: a procedure come of age?" Curr Control Clinicals Trials Cardiovasc. Med. 2001, pp. 67-70, vol. 2, No. 2.

Williams, M.R., et al., "Alternative Energy Sources for Surgical Atrial Ablation", J Card Surg, May-Jun. 2004, pp. 201-206, vol. 19.

Wu, T.J., et al., "Pulmonary veins and Ligament of Marshall as sources of rapid activations in a canine model of sustained atrial fibrillation", 2001.

Yasuda, T., et al., "Predictors of successful catheter ablation of atrial fibrillation using the pulmonary vein isolation technique", J. Cardiol, Aug. 2004, pp. 53-58, vol. 44, No. 2.

Yuda, S., et al., "Long-term follow-up of atrial contraction after the maze procedure in patients with mitral valve disease", J Am Coll Cardiol., 2001, pp. 1622-1627, vol. 37.

* cited by examiner

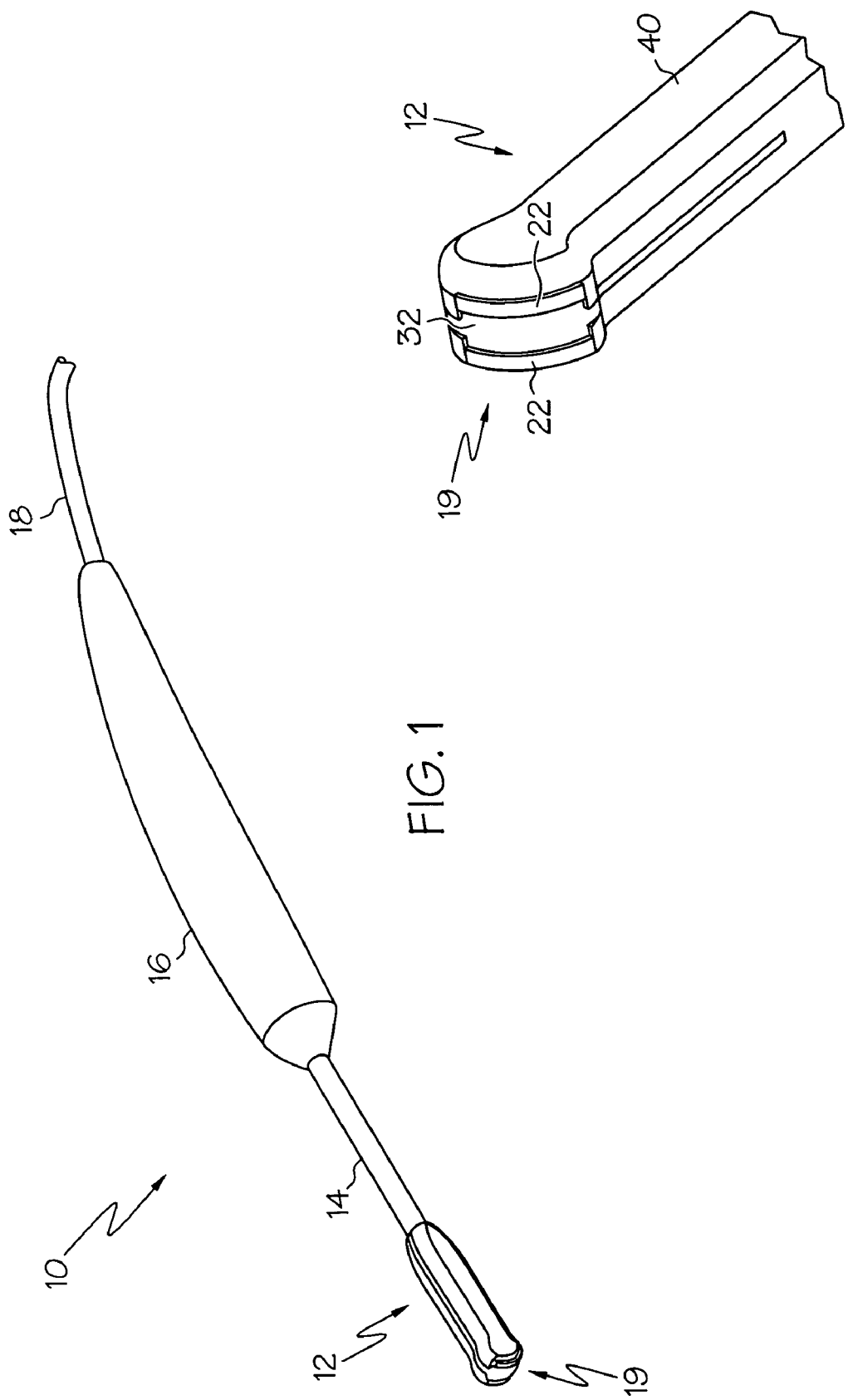

SURGICAL ABLATION AND PACING DEVICE

PRIORITY

This application is a continuation-in-part of U.S. Non-Provisional patent application Ser. No. 11/037,543, filed Jan. 18, 2005 now abandoned, entitled "Surgical Ablation Device," the disclosure of which is incorporated by reference herein. This application also claims priority to U.S. Provisional Patent Application Ser. No. 60/699,679, filed Jul. 15, 2005, entitled "Ablation Device with Sensor," the disclosure of which is incorporated by reference herein.

BACKGROUND

The present invention relates to surgical instruments, with examples relating to cardiovascular pacing devices, systems for controlling such devices, and methods for using such devices. "Surgery" generally refers to the diagnosis or treatment of injury, deformity, disease, or other conditions. In a variety of surgical procedures, it may be desirable to stimulate the heart using a pulsed current via a bi-polar probe or other device. Such pacing may be desirable, for instance, after an ablation procedure has been performed on a heart in order to determine how successful the ablation was. Accordingly, it may be desirable to provide a device operable for use in both ablation and pacing procedures. The foregoing examples are merely illustrative and not exhaustive. While a variety of techniques and devices have been used to pace the heart of a patient or perform other procedures, it is believed that no one prior to the inventors has previously made or used an invention as described in the appended claims.

BRIEF DESCRIPTION OF DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 1 illustrates a perspective view of an example of an ablation device;

FIG. 2 illustrates a perspective detailed view of the head of the ablation device of FIG. 1;

DETAILED DESCRIPTION

Figure 3:
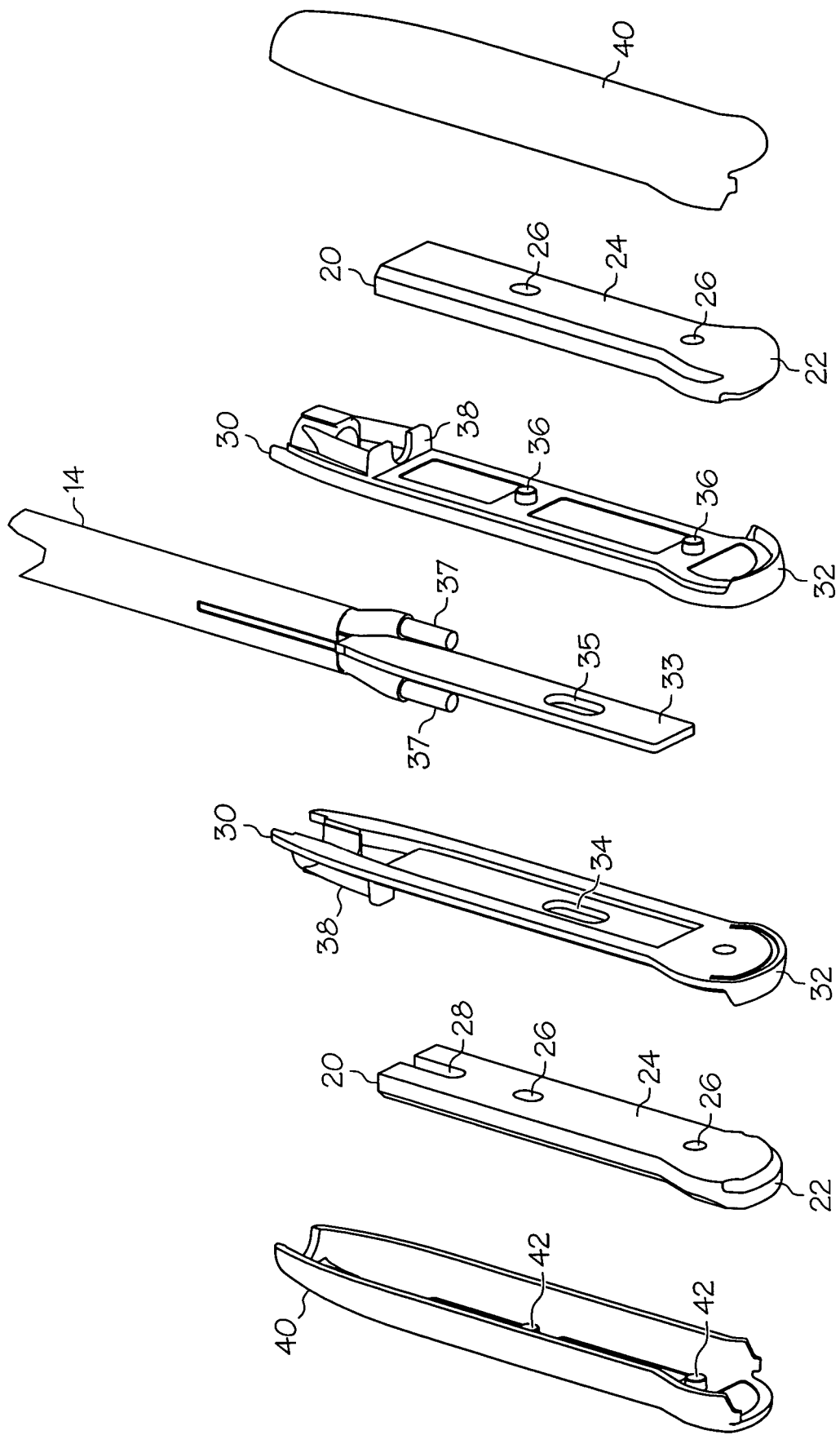
FIG. 3 illustrates an exploded view of the head of the ablation device of FIG. 1.

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIG. 1 illustrates an example of an ablation device (10). The ablation device (10) in this embodiment comprises a handheld wand. The ablation device (10) includes a head (12) connected to the distal end of a shaft (14), and a handle (16) connected to the proximal end of the shaft (14). As shown here, the shaft (14) is straight and substantially rigid; however, flexible, curved, malleable, articulated, or other shafts could also be used depending on a variety of considerations. A power source (not shown) is connected to the cord (18) in the present example.

FIG. 2 illustrates an more detailed view of the head (12) of the ablation device (10). The head (12) includes a tip portion (19) having two electrodes (22), which are capable of being energized with bi-polar energy. In the present example, each electrode (22) includes a smooth surface area for contacting tissue. Each electrode (22) is slender in the sense that the length of the tissue contacting surface is at least 4 times its width. As shown in the present example, the length is between about 5 to 7 times the width. Of course, any other suitable configuration for electrodes (22) may be used.

The electrodes (22) in this example are substantially parallel to one another, and as shown here the electrodes (22) are spaced between about 2 to 4 mm from one another. It will be appreciated, however, that these dimensions are merely exemplary. An electrically insulative surface (32) is interposed between the electrodes (22). In this example, the surface (32) is convex between the electrodes (22), distally extending about 0.01 inches from the lateral plane between the electrodes (22). Again, though, any other suitable dimensions may be used. As shown in the figures, a portion of the tip portion (19) of the head (12) is curved along the transverse axis. In the present example, the curved end is an arc with a radius between 0.19 and 0.21 inches. The electrodes (22) and surface (32) have similar curves. An electrically insulative sheath (40) covers other portions of the head (12). Other suitable configurations will be apparent to those of ordinary skill in the art.

Figure 4:
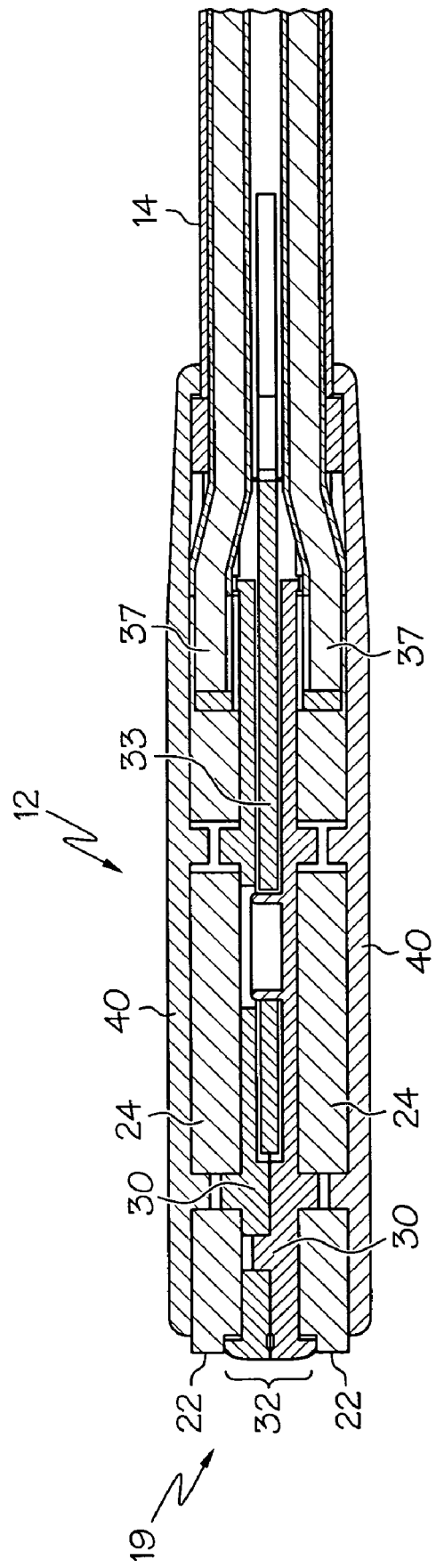
FIG. 4 illustrates a cross-sectional view of the head of the ablation device of FIG. 1.

FIGS. 3 and 4 illustrate some component parts of the head (12) and some related structures. A rib (33) extends distally from the shaft (14). Electrical wires in communication with the cord (18) pass through the shaft (14) and end with electrical terminals (37). A pair of electrical insulators (30) laterally connect to either side of the rib (33). The distal tips of the insulators (30) define the insulative surface (32). A post (hidden in this view) on the right insulator (30) mates with the holes (35, 34). A receiving structure (38) is dimensioned to hold the terminals (37) in their desired positions.

Two conductors (20) laterally connect with the insulators (30). In the present example, each conductor (20) is a contiguous and unitary part; however, two or more components could form the conductor (20). Also in this example, each conductor (20) is a homogeneous material. Each conductor (20) includes an electrode (22) and heat sink (24). Each conductor has a recess (28) dimensioned to snugly receive the corresponding terminal (37), thus facilitating electrical contact with the terminal (37). The sheath (40) covers the assembled head (12). Posts (42, 36) mate with the holes (26) in the conductor (20) to facilitate and maintain alignment of the assembly. The distal ends of the conductors (20), bounded by the surface (32) and the sheath (40), define the surface areas of the electrodes (22).

The conductor (20) in this example is electrically conductive, thus facilitating the flow of current from the terminal (37) to the electrode (22). The conductor (20) in this example is also thermally conductive, thus facilitating the flow of heat from the electrode (22) to the heat sink (24). Some suitable materials for the conductor (22) include, without limitation, copper, silver, gold, platinum, titanium, aluminum, beryllium, nickel, and the like. In one variation, the heat sink (24) is copper while the electrode (22) is gold plated. The heat sink (24) has a volume, which in this example is the volume of the conductor (20). Preferably, the ratio of tissue contacting surface area of the electrode (22) to volume of the heat sink (24) is less than about 3 $in^2/in^3$. In the present example, the ratio is less than about 1 $in^2/in^3$. Any other suitable ratio may be used.

One illustrative use of the device (10) is during surgery to ablate tissue. The surface area of the electrodes (22) are placed in contact with the tissue surface. The electrodes (22) are energized with bi-polar energy by connecting the device (10) to an electric power source. As one with ordinary skill in the art will readily appreciate, RF energy is transmitted to the tissue through the electrodes (22), thus heating the tissue until ablated and a desired lesion is formed in the tissue. Optionally, the head (12) may be swiped over the tissue surface, either laterally or transversely, while maintaining the electrodes (22) in contact with the tissue to ablate larger areas or to ablate the tissue in a desired pattern. Other methods of using the device (10) will be apparent to those of ordinary skill in the art. The heat sink (24) draws heat away from the tissue during the ablation process, thus reducing the temperature elevation of the tissue surface. The temperature reduction may provide the benefit (among other benefits) of facilitating deeper and more controlled lesions, including, when desired, transmural lesions through a tissue wall.

It will be appreciated that creating an ablation in tissue with the device (10) may provide a barrier to electrical signals that may otherwise be communicated across the ablated tissue. By way of example only, such a barrier may provide a form of treating atrial fibrillation or other conditions. For instance, where atrial fibrillation is caused by aberrant or erratic electrical signals coming from one or more pulmonary veins to one or both atria of the heart, an ablation may be provided as a barrier between such veins and atria. In other words, one or more ablations may serve to electrically isolate one or more pulmonary veins from the atria. By preventing or substantially preventing aberrant or erratic electrical signals coming from one or more pulmonary veins from reaching the atria, a more desirable sinus rhythm may be maintained. Of course, any other tissues or anatomical structures may be ablated for any reason.

Figure 5:
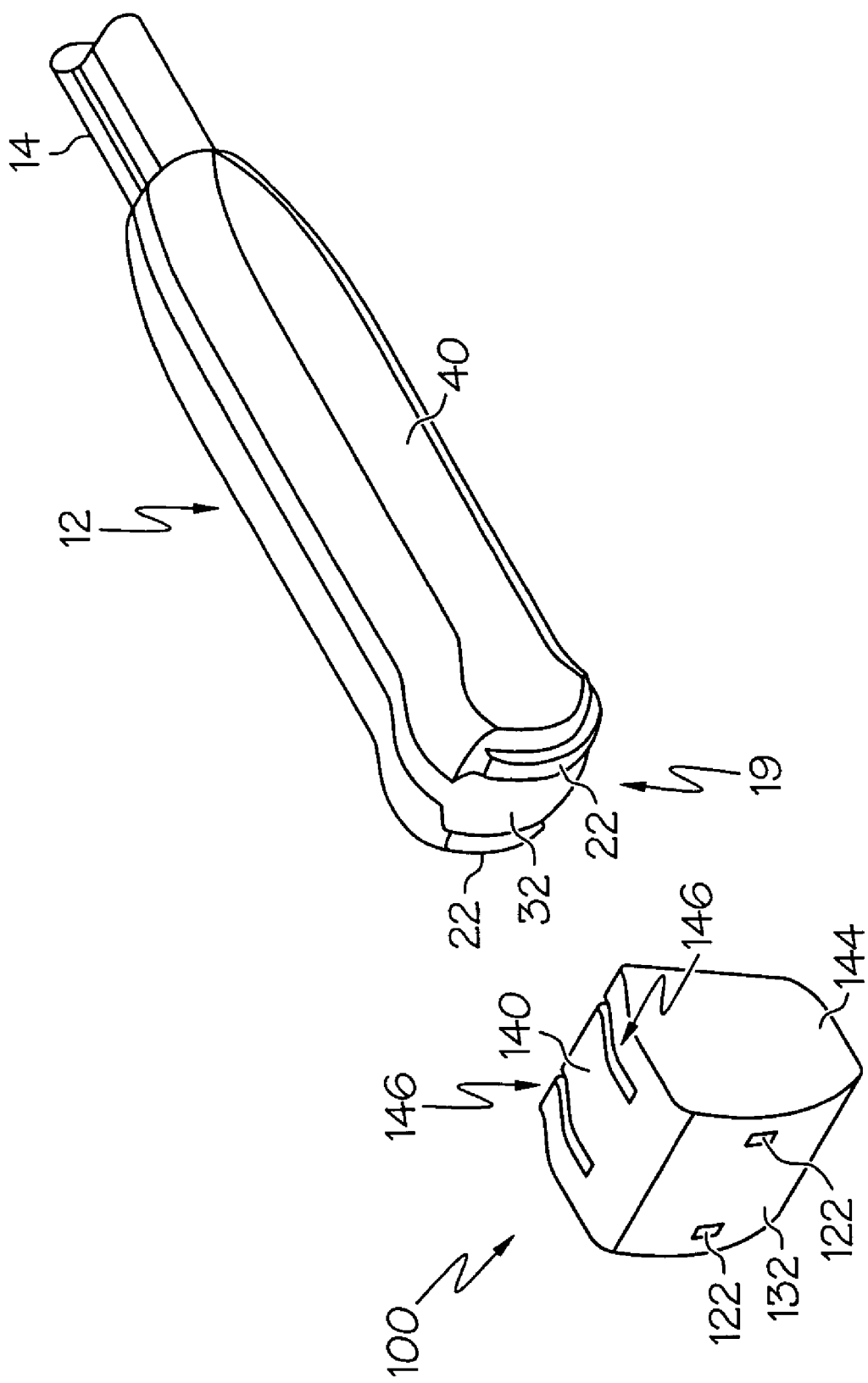
FIG. 5 illustrates a perspective view of an example of a pacing tip configured to engage the head of the ablation device of FIG. 1.
Figure 6:
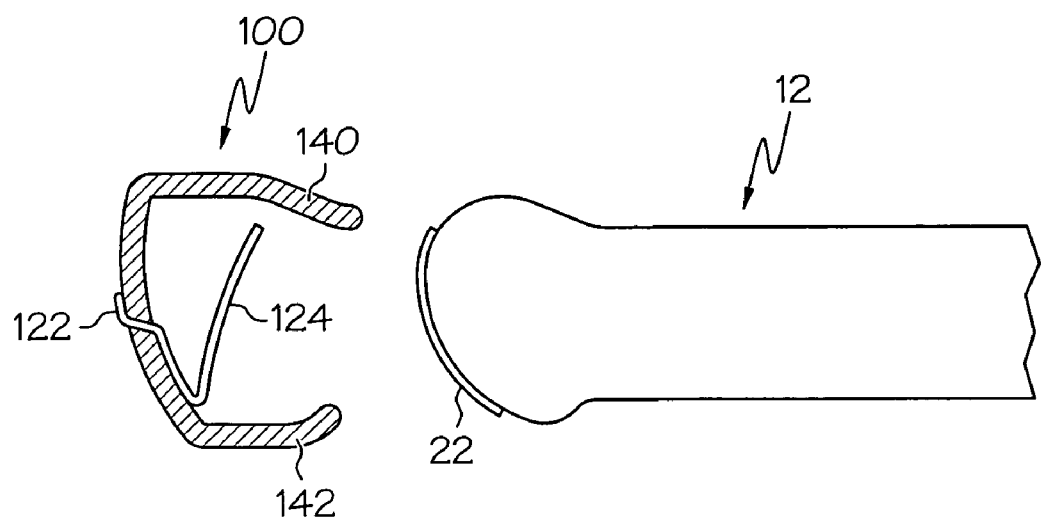
FIG. 6 illustrates a partial cross-sectional view of the pacing tip of FIG. 5 prior to engagement with the head of the ablation device of FIG. 1.
Figure 7:
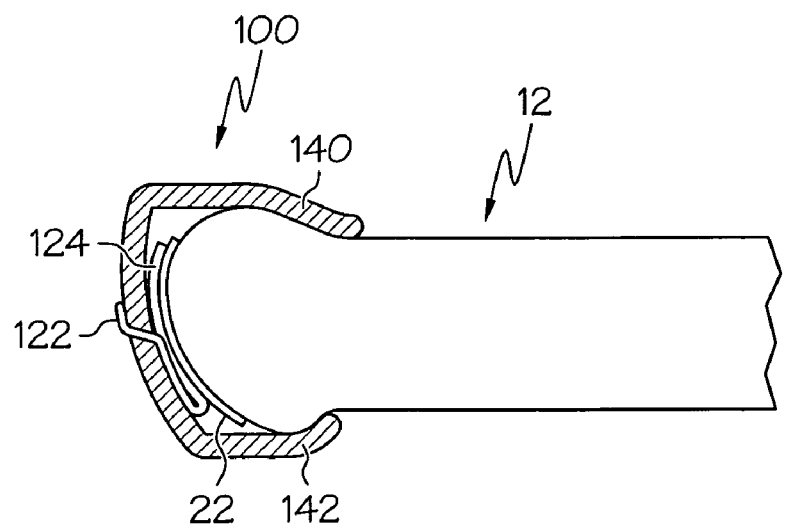
FIG. 7 illustrates a partial cross-sectional view of the pacing tip of FIG. 5 engaged with the head of the ablation device of FIG. 1.

FIGS. 5 through 7 illustrate a pacing tip (100) configured to engage the head (12) of the device (10). The pacing tip (100) comprises a pair of electrodes (122), an insulative face (132), an upper clipping portion (140), a lower clipping portion (142), and a pair of sidewalls (144) extending between the upper and lower clipping portions (140, 142). The upper clipping portion (140) comprises a pair of gaps (146), which are configured to permit some motion of upper clipping portion (140) relative to sidewalls (144). Such gaps (146) may facilitate engagement and disengagement of pacing tip (100) with the head (12) of the device (10). Each of the electrodes (122) comprises a respective leaf spring portion (124). As shown in FIGS. 6 and 7, the upper and lower clipping portions (140, 142) are configured to "snap on" to the head (12) of the device (10). Each of the leaf spring portions (124) is configured to engage a respective electrode (22) on the head (12) when the pacing tip (100) is snapped onto the head (12). The leaf spring portions (124) are further configured to provide electrical continuity between the electrodes (22) of the head (12) and the electrodes (122) of the pacing tip (100). It will be appreciated that, to the extent that the electrodes (122) of the pacing tip (100) are not aligned with the electrodes (22) of the head (12), the leaf spring portions (124) may still be configured to provide electrical continuity between the electrodes (122, 22). It will also be appreciated that leaf spring portions (124) are not necessarily required, and that any other suitable structures or features configured to provide electrical continuity between the electrodes (122, 22) may be used.

As shown, the electrodes (122) of the pacing tip (100) are spaced apart further than the electrodes (22) of the head (12). For instance, the electrodes (122) may be spaced anywhere from approximately 2 mm apart to approximately 5 mm apart. In the present example, the electrodes are spaced apart approximately 3 mm. Of course, any other suitable electrode (122) spacing may be used. In addition, the electrodes (122) of the pacing tip (100) of the present example are each relatively narrower and shorter than the corresponding electrodes (22) on the head (12). It is contemplated that a variety of pacing tips (100) may be made and used having a variety of electrode (122) spacings, dimensions, and configurations. A few of such alternative electrode (122) configurations will be described in greater detail below. It is further contemplated that such a variety of pacing tips (100) may all be similarly engageable with the head (12), providing a modular selection of pacing tips (100) available for user selection based on ideal electrode (122) configurations for a particular use or based on other considerations.

In one exemplary use, the pacing tip (100) is secured to the head (12) of the device (10), and the electrodes (122) are positioned on tissue adjacent the pulmonary veins of a patient's heart. As will be described in greater detail below, a pacing signal is then sent to the tissue via the electrodes (122) until an effect on the heart of the patient (e.g., an increase in the heartbeat rate) is observed. The pacing tip (100) us then removed from the head (12), and the pacing tip (100) and head (12) are both cleaned. Next, the device (10) is used to ablate tissue between the pulmonary veins and heart atria (e.g., using electrodes (22) as described above), providing an ablation line in the tissue. Of course, such a "line" need not be straight, and may comprise a curve or pattern, etc. The head (12) is then cleaned again, and the pacing tip (100) is snapped back onto the head (12) of the device (10). With the pacing tip (100) secured to the head (12), the electrodes (122) are again positioned on tissue adjacent the pulmonary veins of the patient's heart. For instance, the electrodes (122) may be positioned in approximately the same location at which they were positioned previously during the prior act of pacing. The pacing signal that had previously produced an observed effect on the heartbeat rate of the patient is again sent to the tissue via the electrodes (122). To the extent that the same signal no longer produces the same effect, the success of the ablation may be confirmed. In other words, this subsequent act of pacing may be used to verify whether the ablated tissue provides sufficient electrical resistance. Conversely, if the same pacing signal produces the same effect that it had before (or some other unsatisfactory effect), the ablation steps may be performed again, then checked again with the pacing steps until satisfactory results are achieved.

It will be appreciated that any of the foregoing steps may be varied, substituted, supplemented, or omitted. For instance, the initial step of pacing may be omitted. In addition, the second act of pacing may comprise the use of a pacing signal having properties that differ from the prior pacing signal (e.g., higher voltage, higher frequency, etc.). The success of an ablation may also be checked or verified using any suitable techniques other than pacing. Still other ways in which the exemplary method may be modified will be apparent to those of ordinary skill in the art.

As noted above, the device (10) may be used in a pacing mode to deliver a low frequency signal via the electrodes (122) to verify that the ablation has provided a satisfactory conduction block or other sufficient amount of electrical resistance in the tissue. By way of example only, such pacing may include the stimulation of the tissue with a pulsed current via the electrodes (122) of the pacing tip (100). In the context of use on heart tissue, if the heart does not respond to an initial pulsed current, the current may be increased until the heart responds to the stimulation. A response to stimulation may be detected using, by way of example only, an ECG, visual observation to detect an increase in heart rate, and/or by using any other suitable technique. Accordingly, it will be appreciated that, after placing an ablation line on the tissue, the user may verify sufficient conduction block by showing that the heart does not respond to the stimulus when placed on the other side of the electrically isolated line. By way of example only, the pacing signal may be anywhere from between approximately 1.0 to 2.5 Hz, at approximately 0.5 to 10.0 volts, with a current ranging from approximately 0.1 mA to 20.0 mA, at a 500 ohm load. In one embodiment, a signal is varied between approximately 1 to 2 Hz and approximately 0.5 to 2.0 volts. Other signal parameters suitable for pacing may be used, as will be apparent to those of ordinary skill in the art.

While the present example discusses the use of the device (10) to perform pacing, it will be appreciated that a variety of other devices may be used to perform pacing. In particular, like device (10), these other devices may be capable of performing both ablation and pacing, with or without modification of the structure of such devices. For instance, a bi-polar clamp used for ablation may also be used for pacing. By way of example only, any of the bi-polar clamps disclosed in U.S. Non-Provisional patent application Ser. No. 11/254,075, entitled "Articulated Bi-Polar Clamp," filed Oct. 19, 2005, the disclosure of which is incorporated by reference herein, may be used to perform pacing in a manner similar to that described above.

Figure 8:
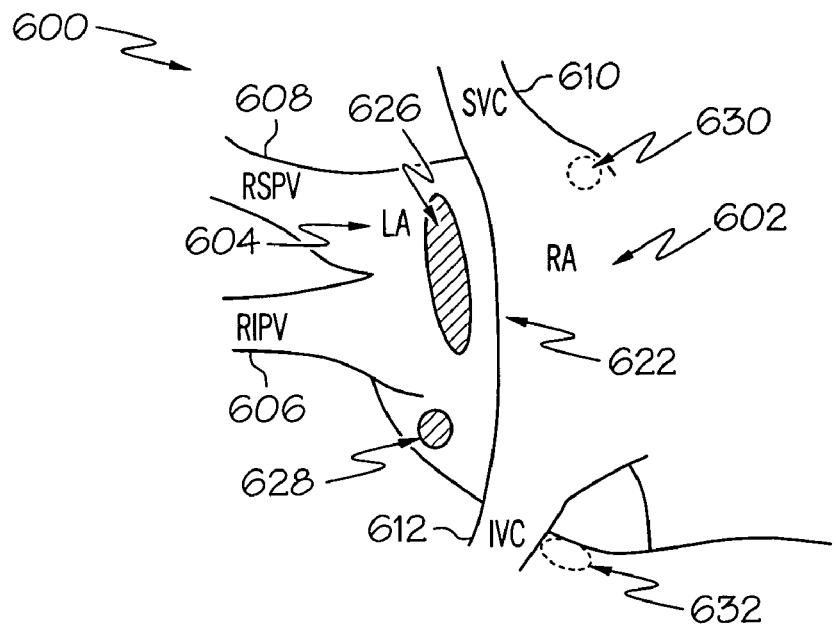
FIG. 8 illustrates a partial left lateral view of a patient's heart.
Figure 9:
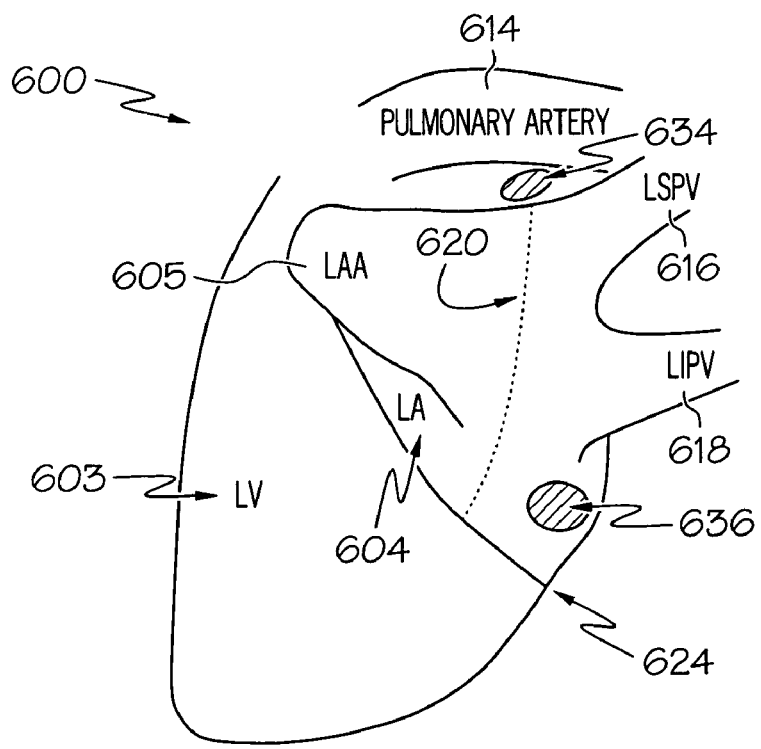
FIG. 9 illustrates a partial right lateral view of the heart of FIG. 8.

In a high frequency stimulation mode, the device (10) may be used to identify specific anatomical structures, including but not limited to terminations of the sympathetic and parasympathetic nervous systems located in the fat pads on and around the heart. Examples of such structures are shown in FIGS. 8 and 9, which depict portions of a heart (600). In particular, FIG. 8 shows the right atrium (602) with superior vena cava (610) and inferior vena cava (612); the left atrium (604) with right superior pulmonary vein (608) and right inferior pulmonary vein (606); and Waterston's groove (622). FIG. 9 shows the left ventricle (603), the left atrium (604) with left atrial appendage (605), left superior pulmonary vein (616), left inferior pulmonary vein (618), and Ligament of Marshall (620); and pulmonary artery (614). FIGS. 8 and 9 also depict autonomic ganglia, which are present on the epicardial surface of the right atrium (602) and left atrium (604), and comprise the anterior right ganglionated plexus (626), the superior left ganglionated plexus (634), the inferior right ganglionated plexus (628), the inferior left ganglionated plexus (636), the SVC-RA ganglionated plexus (630), and the crux ganglionated plexus (624). As shown, the anterior right ganglionated plexus (626) is located anterior to the right pulmonary veins (606, 608). The superior left ganglionated plexus (634) is located between the superior surface of the left atrium (604) (near the base of the left superior pulmonary vein (616)) and the pulmonary artery (614), in close proximity to the site of insertion of the Ligament of Marshall (620) into the pericardium. The inferior right ganglionated plexus (628) is located inferior to the right inferior pulmonary vein (606), at the bottom of the antrum of the right pulmonary veins (606, 608). The inferior left ganglionated plexus (636) is located inferior to the left inferior pulmonary vein (618), at the bottom of the antrum of the left pulmonary veins (616, 618). The SVC-RA ganglionated plexus (630) is located at the medial aspect of the junction of the superior vena cava (610) and right atrium (602). The crux ganglionated plexus (624) is located at the crux of the heart (600) between the right atrium (602) and left atrium (604), close to the coronary sinus ostium (not shown) and inferior vena cava (612). Those of ordinary skill in the art will appreciate that the locations of the ganglionated plexi (626, 628, 630, 632, 634, 636) may vary somewhat relative to FIGS. 8 and 9 for a given patient. Furthermore, it will be appreciated that, using high frequency stimulation, the device (10) may be used to identify or localize these ganglionated plexi (626, 628, 630, 632, 634, 636).

By way of example only, the stimulation signal used to identify the ganglionated plexi (626, 628, 630, 632, 634, 636) may be anywhere from between approximately 13 to 25 Hz, at approximately 1 to 12 volts, with a current ranging from 2 to 24 mA, at a 500 ohm load, with a pulse width between approximately 0.02 and 9 ms. In one embodiment, a signal is varied between approximately 15 to 20 Hz at approximately 10 volts. Other signal parameters suitable for stimulation may be used, as will be apparent to those of ordinary skill in the art. When administered close to or adjacent to a ganglionated plexus (626, 628, 630, 632, 634, or 636), a stimulation signal may produce a vagal response identified by a marked lengthening of the R-R interval during atrial fibrillation.

Having identified any of the ganglionated plexi (626, 628, 630, 632, 634, 636) using stimulation with the device (10), the device (10) may then be used to ablate any or all of the identified ganglionated plexi (626, 628, 630, 632, 634, 636). Endocardial ablation at or near such sites may eliminate the vagal response to stimulation and high frequency fractionated potentials in such areas during stimulation. Ablation of the Ligament of Marshall (620) may also reduce the likelihood of atrial fibrillation. Other suitable ablations sites will be apparent to those of ordinary skill in the art. Similarly, other anatomical structures that may be identified by stimulation with device (10) will be apparent to those of ordinary skill in the art.

In a sensing mode, rather than being used to deliver a signal to the heart, the device (10) is used to measure small signal electrograms at various points on the heart. These may be low frequency, low amplitude signals. To the extent that these signals may vary by location on the heart, it will be appreciated that a point contact may offer sufficient spatial resolution to discriminate between various signals. A sensing mode may therefore permit a user to identify the approximate location of particular anatomical structures or features based on sensed signals received through the device (10). Sensing (e.g., with device (10)) may also be useful in assessing the performance of a conduction block (e.g., one created through ablation with device (10)). For instance, prior to ablation, electrodes (122) may be placed on an area to be isolated through ablation, and the signal sensed at the area may be noted or recorded. After the area is isolated through ablation, the electrodes (122) may again be placed on the same area and compare the sensed signal reading to the one noted or recorded prior to ablation. By way of example only, where pulmonary veins (606, 608, 616, or 618) are conductively isolated through ablation, electrodes (122) may be placed on such pulmonary veins (606, 608, 616, or 618) after the ablation to see of electrical activity of the corresponding atrium (604 or 604) can be sensed. The success of the ablation may be judged by the degree to which the electrical activity of the atrium (604 or 604) can be sensed in the corresponding pulmonary veins (606, 608, 616, or 618). Other suitable targets for sensing, and ways in which sensing may be used, will be apparent to those of ordinary skill in the art.

In one example, the spacing between electrodes (122) on pacing tip (100) for use during sensing is approximately 2 mm. Of course, and other suitable spacing for electrodes (122) may be used. Similarly, any other suitable method for identifying the approximate location of particular anatomical structures or features may be used.

Where the device (10) is in communication with a power source (not shown) via the cord (18), the power source may comprise a user interface operable to receive user input indicating a particular task that the user intends to perform with the device (10). The power source may then communicate an appropriate signal to the electrodes (22, 122) in accordance therewith. Alternatively, the device (10) and/or power source may comprise a logic that is configured to detect the presence of a particular tip (e.g., the pacing tip (100)) secured to the head (12) of the device (10), and may automatically vary the signal based on the detected tip. One exemplary power source that may be used with the device (10) is described in U.S. Provisional Patent Application Ser. No. 60/699,664, entitled "Matrix Router," filed Jul. 15, 2005, the disclosure of which is incorporated by reference herein. In yet another version, a user interface is provided on the device (10) for a user to select a particular mode of use. To the extent that a user interface is used, regardless of its location, the user interface may be operable to provide to the electrodes (22, 122) a signal having suitable parameters for a particular mode of use indicated by the user through the user input.

In another embodiment, the device (10) is configured such that the electrodes (22) may be used for both ablation and pacing, such as by merely changing the power output to the electrodes (22). It will therefore be appreciated that pacing and ablation may both be provided without the need to remove or secure a separate tip (e.g., the pacing tip (100) of FIGS. 5-7) from or to the head (12) of the device (10). Similarly, the electrodes (22) may be configured to permit use for all of ablation, pacing, stimulation, sensing, and any other tasks.

In yet another embodiment, the device (10) is varied such that the electrodes (122) of the pacing tip (100) are integral with the head (12). In one version of this embodiment, a separate ablation tip (not shown) is configured to selectively engage the pacing tip (100), such as by snapping onto the pacing tip (100) portion of the head (12). Such a separate ablation tip may also comprise a functional equivalent to the leaf spring portions (124) to provide electrical continuity between the pacing electrodes (122) and the ablation electrodes (22). In another version of this embodiment, the head (12) comprises two or more pairs of electrodes, each pair being dedicated to a particular task. For instance, a first pair of electrodes (22) may be dedicated to ablation, with a second pair of electrodes (122) being dedicated to pacing. In this version, the device (10) may be operable to electrically address a particular pair or set of electrodes (e.g., 22 or 122) in accordance with selections made by a user. By way of example only, such electrode selections may be made by a user via a user interface on the device (10) or a user interface on a separate control unit. Electrode selections may also be provided automatically based on a user's selection of a task to be performed via a user interface.

A few non-exhaustive examples of alternative tip designs are shown in FIGS. 10-13. Any of these alternative tip designs may be implemented integrally with the head (12), or may be provided in a removable tip (e.g., similar to pacing tip (100)).

Figure 10:
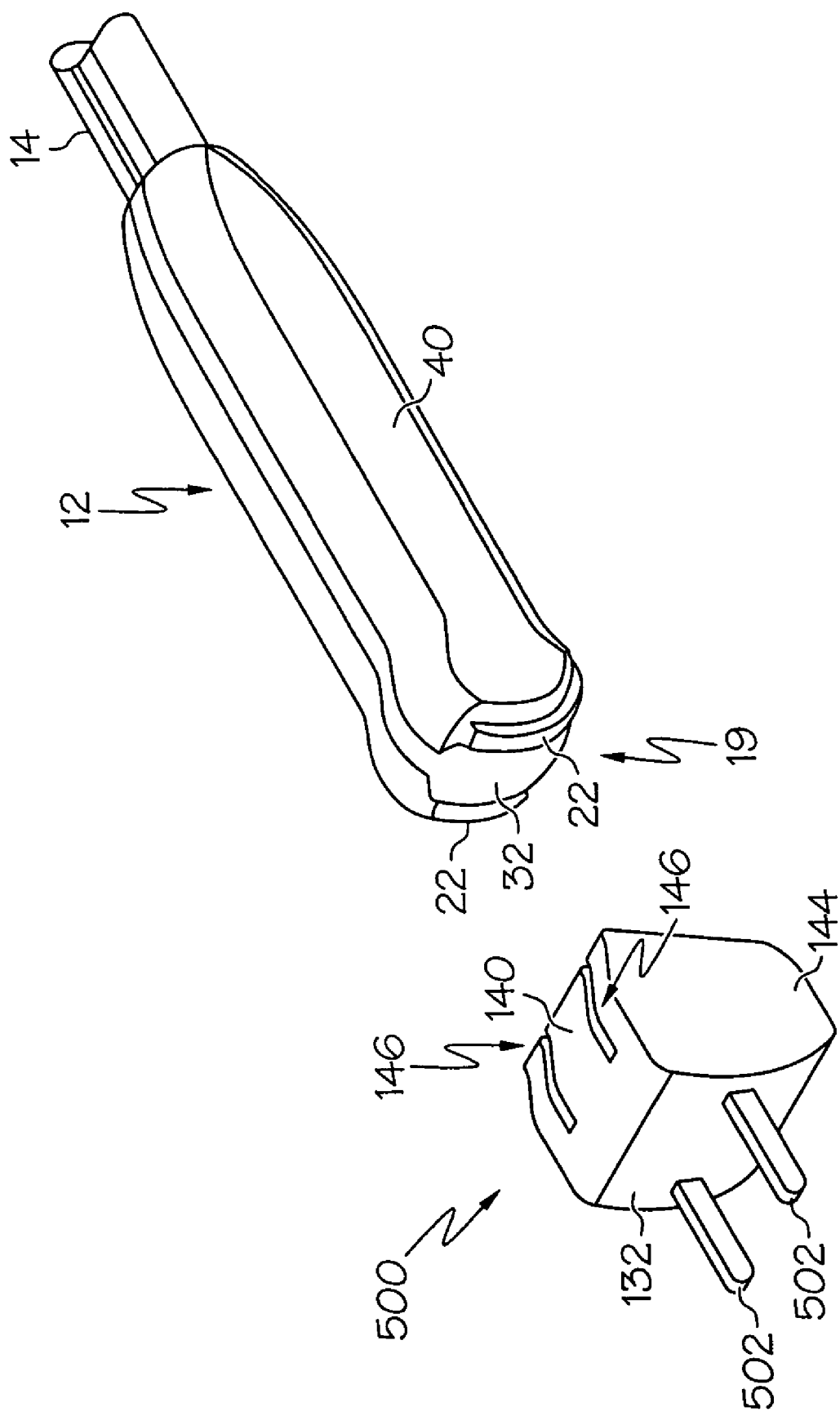
FIG. 10 illustrates a perspective view of an alternative head tip configured to engage the head of the ablation device of FIG. 1.

FIG. 10 shows a tip (500) having a pair of electrode prongs (502). In this embodiment, electrode prongs (502) are operable in a manner similar to electrodes (22 or 122) described above, with the difference being that electrode prongs (502) extend substantially from face (132) of tip (500). Thus, it will be appreciated that electrode prongs (502), or any suitable variation thereof, may be used to ablate, pace, sense, stimulate, or perform any other task. It will also be appreciated, particularly where electrode prongs (502) are substantially integral with head (12), that extension of electrode prongs (502) may be adjustable (e.g., via a lever, slider, or other input in handle 16). A user may therefore selectively adjust the amount of extension of electrode prongs (502) as desired.

Figure 11:
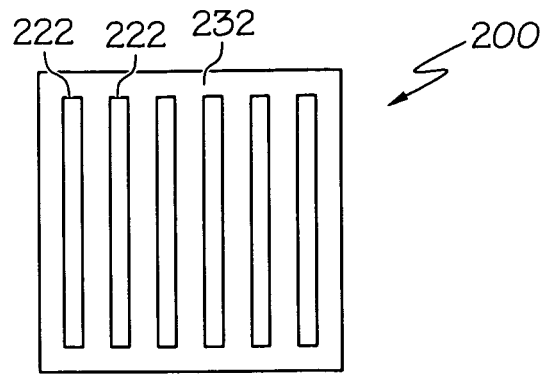
FIG. 11 illustrates a frontal view of an alternative head tip that may be used in addition to or in lieu of the head tips of FIGS. 1-7 or 10.
Figure 12:
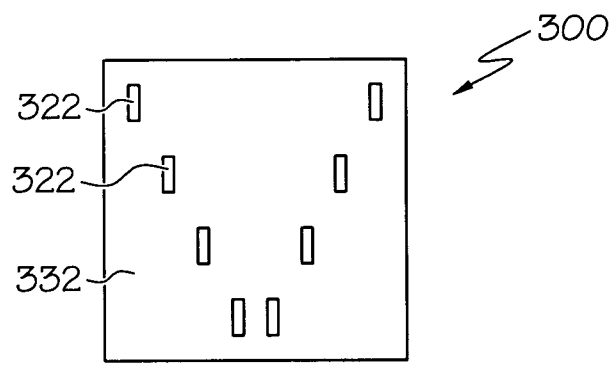
FIG. 12 illustrates a frontal view of an alternative head tip that may be used in addition to or in lieu of the head tips of FIGS. 1-7 or 10-11.
Figure 13:
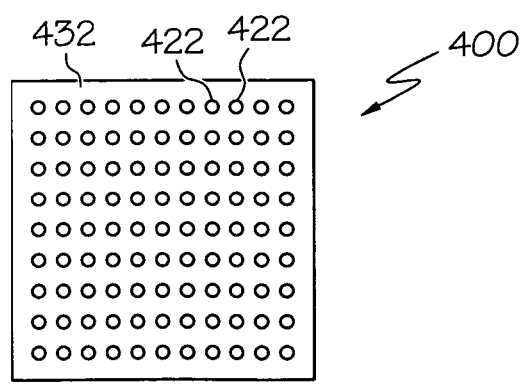
FIG. 13 illustrates a frontal view of an alternative head tip that may be used in addition to or in lieu of the head tips of FIGS. 1-7 or 10-12.

FIG. 11 shows a tip (200) having a plurality of electrodes (222) disposed about a non-conductive face (232). FIG. 12 shows another tip (300) having a plurality of electrodes (322) disposed about a non-conductive face (332). FIG. 13 shows yet another tip (400) having a matrix or array of electrodes (422) disposed about a non-conductive face (432). It will be appreciated that each electrode (222, 322, 422) may extend from their respective face (232, 332, 432) to a degree similar to the extension of electrodes (122) from face (132) (e.g., generally co-planar with face (132) or a few millimeters from face (132)). Alternatively, each electrode (222, 322, 422) may extend substantially from their respective face (232, 332, 432) in a manner similar to the extension of electrode prongs (502) from face (132) of tip (500). Other suitable degrees of extension will be apparent to those of ordinary skill in the art.

It will also be appreciated that, in the versions shown in FIGS. 11-13, each electrode (222, 322, 422) of a plurality may be individually electrically addressable (e.g., in accordance with user selections or automatic selections). It will also be appreciated that electrodes (222, 322, 422) may be addressable in pairs or sets. Suitable structures and techniques for addressing electrodes (222, 322, 422), as well as selections of electrodes (222, 322, 422) for being addressed in particular circumstances, will be apparent to those of ordinary skill in the art. In addition, it will be appreciated that any other suitable number or configuration of electrodes may be used.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A surgical device for ablating tissue and pacing a heart using electrical energy, the device comprising:
   a) a handle;
   b) a head connected to the handle, wherein the head has a transverse axis and comprises a first tip portion having a distal-facing surface convexly-curved relative to the transverse axis, wherein the first tip portion comprises a first pair of convexly-curved electrodes on the surface thereof adapted to contact tissue and operable to communicate an electrical signal;
   c) a pair of conductors, wherein each conductor is in communication with a respective one of the pair of electrodes of the first tip portion, wherein each of the conductors is configured to selectively deliver either pacing signals or ablation energy from a power source to tissue; and
   d) a second tip comprising a second pair of electrodes on the surface thereof adapted to contact tissue for the delivery of pacing signals, wherein the second tip is configured to be removably secured to the head, wherein the first pair of electrodes conducts electrical signals to the second pair of electrodes when the second tip is secured to the head.

2. The surgical device of claim 1, wherein the head is connected to the handle via a malleable shaft.

3. The surgical device of claim 2, wherein a portion of the pair of conductors is located within the malleable shaft.

4. The surgical device of claim 1, wherein the electrodes of one or both of the first tip portion or the second tip are configured to ablate tissue in accordance with an electrical signal communicated through the conductors.

5. The surgical device of claim 1, wherein the electrodes of one or both of the first tip portion or the second tip are configured to pace a heart in accordance with an electrical signal communicated through the conductors.

6. The surgical device of claim 1, wherein the electrodes of the first tip portion are configured to ablate tissue in accordance with an ablation signal communicated through the conductors, wherein the electrodes of the second tip are configured to pace a heart in accordance with a pacing signal communicated through the conductors.

7. The surgical device of claim 1, wherein each electrode of one or both of the first tip portion or the second tip is parallel with the other electrode of the corresponding pair.

8. The surgical device of claim 1, wherein each of the electrodes of the second tip are in communication with a respective leaf spring, wherein each of the leaf springs is configured to provide electrical continuity between the head and the electrodes of the second tip when the second tip is secured to the head.

9. The surgical device of claim 8, wherein each of the leaf springs is configured to engage a corresponding electrode of the first tip portion.

10. The surgical device of claim 1, wherein the second tip is configured to snap onto the head adjacent to the first tip portion.

11. The surgical device of claim 1, wherein one or both of the first tip portion or the second tip comprises an insulative convex surface extending between the corresponding pair of electrodes.

12. The surgical device of claim 1, wherein the electrodes of one or both of the first tip portion or the second tip are bi-polar.

13. The surgical device of claim 1, wherein one or both of the first tip portion or the second tip further comprises a plurality of electrode pairs.

14. The surgical device of claim 1, wherein the electrodes of one or both of the first tip portion or the second tip are further operable to sense electrical signals passing through tissue positioned adjacent to the electrodes.

15. The surgical device of claim 1, further comprising:
   a) a power source operable to communicate electrical signals to the conductors; and
   b) a user interface operable to receive user selections of modes, wherein the selectable modes comprise ablation mode and pacing mode, wherein the user interface is operable to provide a signal to the electrodes of one or both of the first tip portion or second tip in accordance with user mode selections.

16. A surgical device for ablating tissue and pacing a heart using electrical energy, the device comprising:
   a) a handle;
   b) a head connected to the handle, wherein the head has a transverse axis and comprises a first tip portion having a distal-facing surface convexly-curved relative to the transverse axis, wherein the first tip portion comprises a first pair of convexly-curved electrodes on the surface thereof adapted to contact tissue and operable to communicate an electrical signal;
   c) a pair of conductors, wherein each conductor is in communication with a respective one of the pair of electrodes of the first tip portion, wherein each of the conductors is configured to selectively deliver either pacing signals or ablation energy from a power source to tissue;
   d) a second tip comprising a second pair of electrodes on the surface thereof adapted to contact tissue for the delivery of pacing signals, wherein the second tip is configured to be removably secured to the head, wherein the first pair of electrodes conducts electrical signals to the second pair of electrodes when the second tip is secured to the head;
   e) a power source operable to communicate electrical signals to the conductors; and
   f) a user interface operable to detect the presence of the second tip and provide the appropriate pacing or ablation signal to the electrodes of one or both of the first tip portion or second tip.

* * * * *